United States Patent
Pan et al.

(10) Patent No.: US 6,348,187 B1
(45) Date of Patent: Feb. 19, 2002

(54) PEROXIDE/ESSENTIAL OILS CONTAINING MOUTHWASH COMPOSITIONS AND TWO-PART MOUTHWASH SYSTEMS

(75) Inventors: Pauline Pan, Morris Plains; Sau-Hung S. Leung, Parsippany; Michael Rubin, Boonton, all of NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/117,949

(22) PCT Filed: Jan. 13, 1997

(86) PCT No.: PCT/US97/00439

§ 371 Date: Aug. 3, 1998

§ 102(e) Date: Aug. 3, 1998

(87) PCT Pub. No.: WO97/26855

PCT Pub. Date: Jul. 31, 1997

Related U.S. Application Data

(60) Provisional application No. 60/010,508, filed on Jan. 24, 1996.

(51) Int. Cl.[7] .............. A61K 7/16; A61K 7/20; A61K 7/26; A61K 33/40; A61K 35/78
(52) U.S. Cl. .............. 424/53; 424/49; 424/58; 424/616
(58) Field of Search ............ 424/49–58

(56) References Cited

U.S. PATENT DOCUMENTS

| | | | |
|---|---|---|---|
| 4,431,631 A | * 2/1984 | Clipper et al. | 424/53 |
| 4,523,589 A | * 6/1985 | Krauser | 128/203.27 |
| 4,537,778 A | * 8/1985 | Clipper et al. | 424/53 |
| 4,684,517 A | * 8/1987 | Clipper et al. | 424/53 |
| 4,900,721 A | * 2/1990 | Bansemir et al. | 424/49 |
| 4,925,655 A | * 5/1990 | Smigel et al. | 424/53 |
| 4,945,087 A | * 7/1990 | Talwar et al. | 424/49 |
| 4,980,152 A | * 12/1990 | Frazier et al. | 424/53 |
| 5,085,853 A | * 2/1992 | Williams et al. | 424/53 |
| 5,174,990 A | * 12/1992 | Douglas | 424/53 |
| 5,186,926 A | * 2/1993 | Williams et al. | 424/53 |
| 5,188,822 A | * 2/1993 | Viccaro et al. | 424/52 |
| 5,298,238 A | * 3/1994 | Hussein et al. | 424/49 |
| 5,310,546 A | * 5/1994 | Douglas | 424/53 |
| 5,416,075 A | * 5/1995 | Carson et al. | 514/23 |
| 5,486,304 A | * 1/1996 | Euga et al. | 252/99 |
| 5,817,295 A | * 10/1998 | Chaudhari et al. | 424/49 |
| 5,891,422 A | * 4/1999 | Pan et al. | 424/49 |
| 5,908,612 A | * 6/1999 | Dailey et al. | 424/49 |
| 5,945,087 A | * 8/1999 | Nelson et al. | 424/49 |
| 5,945,088 A | * 8/1999 | Delli Santi et al. | 424/49 |
| 6,010,993 A | * 1/2000 | Romano et al. | 510/309 |
| 6,048,836 A | * 4/2000 | Romano et al. | 510/490 |

FOREIGN PATENT DOCUMENTS

| | | | |
|---|---|---|---|
| EP | 0803243 | * | 10/1997 |
| WO | 95/34276 | * | 12/1995 |
| WO | 96/16633 | * | 6/1996 |
| WO | 96/29047 | * | 12/1996 |
| WO | 97/13495 | * | 4/1997 |
| WO | 97/26855 | * | 7/1997 |
| WO | 97/30685 | * | 8/1997 |

OTHER PUBLICATIONS

Sperry Journal of Forensic Science 35(5):1138–1142 Fatal Ethanol Intoxication from Household Products Not Intended for Ingestion (F16.1 p. 1140–Listerine 26.9% ethanol), Sep. 1990.*

* cited by examiner

*Primary Examiner*—Shep K. Rose
(74) *Attorney, Agent, or Firm*—Darryl C. Little; Evan J. Federman

(57) ABSTRACT

An antimicrobial mouthwash composition that is useful in the prevention and reduction of bad breath, plaque and related gum diseases comprises an antimicrobial effective amount of thymol and one or more other active essential oils; optionally, ethanol in an amount up to about 30% v/v; from about 0.1% to about 8.0% w/v of a peroxide; at least one surfactant in an amount sufficient to solubilize the essential oils; and water. The compositions may be reduced alcohol or alcohol-free compositions. Further a two-part mouthwash system is disclosed, comprising a base composition and a peroxide solution which may be mixed to form an antimicrobial mouthwash composition. The actives not only provide enhanced efficacy but are completely solubilized, thus providing an aesthetically appealing product.

20 Claims, No Drawings

US 6,348,187 B1

PEROXIDE/ESSENTIAL OILS CONTAINING MOUTHWASH COMPOSITIONS AND TWO-PART MOUTHWASH SYSTEMS

CROSS REFERENCE

This application is a national stage application under Title 35, United States Code 371 of PCT/US97/00439 filed Jan. 15, 1997, which claims priority under Title 35, United States Code 119(e) to Provisional Application Ser. No. 60/010,508, filed Jan. 24, 1996.

BACKGROUND OF THE INVENTION

1. Field of the Invention

The invention relates generally to mouthwashes for the prevention and elimination of bad breath as well as for the reduction of oral microorganisms resonsile for the development of dental plaque and tooth decay. Dental plaque can lead to the formation of calculus, gingivitis and other related gum diseases. In particular, the present invention relates to a mouthwash which is effective in preventing these problems and which contains both hydrogen peroxide and one or more essential oils (hereinaer referred to as "a hydrogen peroxide/essential oils containing mouthwash". The mouthwash may be a high alcohol mouthwash (e.g., containing up to about 25–30% by volume of alcohol), a reduced alcohol mouthwash or an alcohol-free mouthwash with the reduced alcohol mouthwash being particularly preferred. The invention also relates to a two-part mouthwash system for delivering and preparing the mouthwashes of this invention.

2. Description of Related Art

Oral rinse and mouthwash compositions have been used by people for many years for the prevention of bad breath and for the elimination of bacteria and other oral microorganisms that are responsible not only for bad breath but also tooth decay, plaque and gum diseases such as gingivitis and periodontitis. To this end, antiseptic mouthwashes in the past have been designed to clean the oral cavity, provide fresh breath and kill these pathogenic microbes.

Thymol, a well known antiseptic compound also known as an essential oil, is utilized for its antimicrobial activity in a variety of mouthwash preparations. In particular, thymol can be utilized in oral hygiene compositions such as mouth rinses in sufficient quantities to provide desired beneficial therapeutic effects. Listerine®-brand mouthwash is a well-known antiseptic mouthwash that has been used by millions of people for over one hundred years and has been proven effective in killing microbes in the oral cavity that are responsible for plaque, gingivitis and bad breath. Thymol, together with other essential oils such as methyl salicylate, menthol and eucalyptol, are active ingredients in antiseptic mouth rinses such as Listerine®. These oils achieve their efficacy although present in small amounts. Without being restricted to any specific theory, it is now believed that the efficacy and taste of antiseptic mouthwashes such as Listerine® may be due to the dissolution of these four active ingredients. Dissolution is also important from an aesthetic point of view since a clear mouthwash solution is certainly preferred by consumers to one that is cloudy, turbid or heterogeneous.

The leading antiseptic mouthwashes have always contained alcohol (i.e., ethanol) at fairly high levels, ranging from approximately 25 up to about 30% by volume, based on the total mouthwash volume (hereinafter referred to as "% v/v"). Alcohol is used both as a vehicle and as a solvent in which the active ingredients, and additives such as astringents, fluorides, color additives, flavor oils, and the like, can be dissolved and then dispersed into solution. Alcohol also provides a preservative role for the mouthwash during storage and use, and enhances the flavor oil organoleptic cues.

However, the use of high levels of alcohol has been recently challenged from an overall health standpoint, even though clinical data have not proven adverse health risk effects.

Merely reducing the levels of alcohol in these mouthwash compositions, however, has significant disadvantages. It has been found that lower alcohol levels result not only in a loss in the solubility of the actives and other ingredients in the composition, but there is also a noticeable decrease in the ability of the composition to kill the oral microorganisms responsible for bad breath, plaque and gum disease.

Hydrogen peroxide has been employed in alcohol and alcohol-free mouthwash compositions. While hydrogen peroxide is a known bactericide, it is not universally antiseptic and therefore its anti-plaque efficacy is suspect. Thus, a mouthwash composition containing anti-plaque effective essential oils and hydrogen peroxide which results in improved anti-plaque efficacy over compositions containing essential oils alone would be unexpectedly advantageous. Moreover, there is a substantial need for the development of a reduced alcohol mouthwash in which the essential oils are completely dissolved and that continues to be effective in the prevention of bad breath the killing of oral microbes and the resultant reduction or elimination of plaque.

The prior art reflects a number of attempts at formulating hydrogen peroxide-containing reduced alcohol and alcohol-free mouthwash compositions. For example, U.S. Pat. Nos. 5,310,546 and 5,174,990 disclose a mouthrinse formulation having between about 0.25% and about 0.65% by weight, based on the total volume of the composition (hereinafter referred to as "% w/v"), of hydrogen peroxide, between about 0.005% and about 0.1% w/v zinc chloride, at least about 0.03% w/v sodium lauryl sulfate, at least about 0.006% w/v citric acid, at least about 0.012% w/v sodium citrate and less than about 5% ethanol. The ethanol may be denatured with denaturing agents, generally in an amount less than 0.1% of the mouth rinse. The disclosed denaturing agents include anethole, anise oil, bay oil, bergamot oil, bitter almond oil, cedar leaf oil, cinnamon oil, clove oil, eucalyptol, eucalyptus oil, eugenol, lavender oil, menthol, peppermint oil, sassafras oil, spearmint oil, terpeneless spearmint oil, thyme oil, thymol and wintergreen oil, alone or in combination.

U.S. Pat. No. 4,900,721 discloses an aqueous disinfectant for disinfecting the skin and mucous membranes. The disinfectant may comprise 8 to 25% by weight ethanol, based on the total weight of the composition (hereinafter referred to as "% w/w"), 0.2 to 0.7% w/w hydrogen peroxide, 0.1 to 0.5% w/w of at least one carboxylic acid, such as lactic acid or benzoic acid, 0.05 to 1.0% w/w of at least one microbicidally active nitrogen-containing organic compound, such as chlorhexidine gluconate, 0.01 to 0.2% w/w of a microbicidally active compound, such as an ethereal oil containing 91.4% peppermint oil (90% menthol, 4.0% salicylic acid phenylester, 3.5% anethole, 0.6% eugenol and 0.5% thymol) and the balance water. This reference alleges that antimicrobial phenolic compounds produce a synergistic antimicrobial effect when combined with the other compounds. The reference also discloses adding an emulsifier at a ratio of 2:1 to 1:2 of the phenolic compound. The microbicidally active, nitrogen-containing organic compound is an essential component of the composition.

U.S. Pat. No. 4,431,631 discloses an oral aqueous solution containing 1 to 3% w/v hydrogen peroxide, 3–15% w/v of a polyhydric alcohol, such as glycerin or sorbitol, 3–10% w/v ethanol, 0.3 to 2% w/v of a nonionic water soluble polyoxyethylenated polyoxypropylene polyol surfactant, 0.3 to 2% w/v of a nonionic surface active water soluble polyoxyethylenated monester of sorbitol with $C_{10-18}$ fatty acid, a sweetener compound and a flavor selected from either (i) a wintergreen flavor containing methyl salicylate and menthol in a weight ratio of about 3:1 to 5:1 and (ii) a cinnamon flavor that is a propylene glycol solution containing about 6–9% menthol, 32–38% cinnamic aldehyde and 6–9% clove oil. This reference alleges that the specifically disclosed flavorants are not adversely affected by the hydrogen peroxide. In U.S. Pat. No. 4,537,778, an aqueous oral composition containing only 1 to 3% w/v hydrogen peroxide and the particular above-described flavorant is disclosed, but not exemplified. This patent describes the other components listed in U.S. Pat. No. 4,431,631 as preferred adjuvants.

U.S. Pat. No. 5,104,644 discloses a mouthrinse preparation having about 0.5 to about 3% w/v of hydrogen peroxide, at least 0.02% w/v zinc chloride, at least about 0.04% w/v sodium lauryl sulfate, at least about 0.08% w/v sodium citrate and about 2 to 3.5% w/v ethanol. Peppermint oil and menthol are used as flavorants. The reference alleges that the composition is capable of killing bacteria associated with dental disease.

U.S. Pat. Nos. 5,302,373 and 5,330,749 disclose a concentrated aqueous ethanolic mouthwash formulation comprised of 5 to 50% w/w ethanol, 5 to 35% w/w water, about 0.5 to 30% w/w of a humectant ingredient and about 2 to 30% w/w of a suspension of particulate alkali met bicarbonate ingredient with an average particle size of about 0.5–5 microns. The concentrate may be diluted with about 0.2 to 4 parts by volume water per part by volume of concentrate. These references disclose that optional bactericides may be selected from, among others, thymol or hydrogen peroxides and that optional flavorants may include, among others, peppermint, wintergreen, eucalyptus or methyl salicylate.

U.S. Pat. No. 5,200,194 is directed to an oral osmotic device for delivering a drug into the mouth of a human patient The reference lists, among many others, ethanol, hydrogen peroxide and non-charged phenolic agents such as thymol as suitable anti-plaque agents. This reference does not suggest or disclose the combination of those agents, particularly in a mouthwash formulation.

Clearly, a hydrogen peroxide/essential oils containing mouthwash having greater anti-plaque efficacy that exhibited by mouthwashes employing essential oils alone would be both unexpected and significantly advantageous. Moreover, a need clearly exists for a reduced alcohol or alcohol-free composition that is highly efficacious in the prevention of bad breath, plaque and gum disease. In addition, there is a need for such oral compositions that both kill the oral microflora responsible for these problems cleaning the oral cavity leaving a fresh, lubricous mouthfeel, and also cleaning teeth.

SUMMARY OF THE INVENTION

The present invention is a hydrogen peroxide/essential oils containing antimicrobial mouthwash composition with a high level of efficacy in the prevention of plaque, gum disease and bad breath, and, in particular, the invention is a reduced alcohol or alcohol-free mouthwash composition. In addition, the antimicrobial oral mouthwash compositions of this invention are clear, aesthetically appealing products.

A high alcohol (up to about 30% v/v of ethanol) peroxide/essential oils containing mouthwash of this invention provides an effective anti-plaque mouthwash composition. However, it is highly preferred to employ the reduced alcohol (up to about 22% v/v of ethanol) mouthwash composition or even the alcohol free (substantially free of ethanol) mouthwash compositions of this invention.

In one embodiment, the present invention provides a hydrogen peroxide/essential oils containing antimicrobial mouthwash composition which comprises: (a) an antimicrobial effective amount of thymol and one or more other essential oils; (b) ethanol in an amount up to about 30% v/v; (c) from about 0.1% to about 8.0% w/v, preferably from about 0.1% to about 3.0% w/v, and most preferably from about 0.1% to about 2.9% w/v, of a peroxide; (d) a sufficient amount of at least one surfactant to assist in the solubilization of said essential oils; and (e) water. The R-Factor (a measure of anti-plaque efficacy, described infra) of said compositions is generally less than about 2.0, preferably less than about 1.2, most preferably less than about 1.0.

A particularly preferred embodiment of the present invention provides a reduced alcohol, antimicrobial mouthwash composition which comprises: (a) an antimicrobial effective amount of thymol and one or more other essential oils; (b) ethanol in an amount of up to about 22% v/v, preferably no more than about 10% v/v; (c) from about 0.1% to about 8.0% w/v, preferably from about 0.1% to about 3.0% w/v, and most preferably from about 0.1% to about 2.9% w/v, of a peroxide; (d) a sufficient amount of at least one surfactant to assist in the solubilization of said essential oils; and (e) water. The preferred peroxide of this invention is hydrogen peroxide, although any peroxide or hydrogen peroxide precursor, e.g., sodium percarbonate, sodium peroxide, chlorine dioxide, other peroxide salts, or in combination may be employed.

In another embodiment, the present invention provides an alcohol-free antimicrobial mouthwash composition which comprises: (a) an antimicrobial effective amount of thymol and one or more other essential oils; (b) from about 0.1% to about 8.0% w/v, preferably from about 0.1% to about 3.0% w/v, and most preferably from about 0.1% to about 2.9% w/v, of a peroxide; (c) a sufficient amount of at least one surfactant to assist in the solubilization of said essential oils; and (d) water. This embodiment is substantially free of ethanol.

Another embodiment of this invention is directed to a peroxide/essential oils containing two-part mouthwash system comprising: (i) a first vessel containing a base composition comprising thymol and one or more essential oils, optionally ethanol, at least one surfactant and water and (ii) a second vessel containing an aqueous peroxide solution. Preferably the resulting mouthwash composition is a reduced alcohol or alcohol-free composition. This two-part mouthwash system helps to ensure the stability of the resulting mouthwash by isolating the other components of the mouthwash from the hydrogen peroxide until just prior to use. The concentration of the components in the base composition and in the peroxide solution are such that upon mixing an amount of the base solution with an amount of the peroxide solution, i.e., a predetermined ratio, a peroxide essential oils containing and preferably a reduced alcohol or alcohol-free mouthwash composition as described above results. The amount of base solution that is mixed with the peroxide solution, i.e., the ratio of the mixture, is predetermined so that concentration of the components in the base solution and aqueous peroxide solution can be adjusted to provide the inventive mouthwash composition upon mixing.

This embodiment of the invention provides an advantageous two-part mouthwash system which can be employed to deliver the mouthwash composition of this invention without stability problems which may result from the mixture of a peroxide with the other active components of the mouthwash composition.

DETAILED DESCRIPTION OF THE INVENTION

The mouthwash compositions of this invention provide an unexpected high degree of antiseptic efficacy towards oral microorganisms responsible for oral malodor and the build-up of plaque and calculus and the resulting tooth and gum diseases that may follow. In particular, the mouthwash compositions of this invention exhibit enhanced antimicrobial efficacy over compositions containing only essential oils or hydrogen peroxide alone. Significantly, these advantageous results are achieved for the mouthwash compositions of this invention even with reduced alcohol content or when they are alcohol-free. Although the exact mechanism of action is unknown, enhanced antimicrobial efficacy is obtained when minor amounts of thymol and one or more other essential oils (e.g., eucalyptol, menthol and methyl salicylate) are combined with about 0.1% to about 8.0%, preferably about 0.1% to about 3.0% w/v of a peroxide and a surfactant in an amount sufficient to solubilize the essential oils. Most preferably the peroxide is employed in an amount of firm about 0.1% to about 2.9% w/v. The preferred peroxide is hydrogen peroxide. However, it is also possible to employ a hydrogen peroxide precursor capable of generating hydrogen peroxide in solution. It is believed that the hydrogen peroxide synergistically enhances the antimicrobial efficacy of the essential oils.

Without being bound to theory, it is believed that the peroxide enhances the efficacy of the antimicrobial composition by causing pore channel formation and/or delipidization of bacterial membranes. It is further theorized that the peroxide may enhance the anti-plaque efficacy of the composition through hydrogen bonding, superoxide formation and/or a synergistic antimetabolic affect with the essential oils. Other potential mechanisms of action resulting in enhanced efficacy may be increased peroxide tension in the saliva and plaque, improved substantivity on the tooth and oral surfs and/or an increased diffusion of the essential oils. These potential mechanisms of action are set forth only as theory and do not in anyway limit the scope of this invention.

Thymol, $(CH_3)_2CHC_6H_3(CH_3)OH$ (isopropyl-m-cresol), is only slightly soluble in water but is soluble in alcohol, and its presence is one of the reasons alcohol was necessary in the well-established, high alcohol commercial mouthwashes such as Listerine®. Methyl salicylate, $(C_6H_4OHCOOCH_3)$, also known as wintergreen oil, additionally provides flavoring to the mouthwash together with its antimicrobial function. Eucalyptol ($C_{10}H_{18}O$; cineole) is a terpene ether and provides a cooling, spicy taste together with its antimicrobial functions. Menthol ($CH_3C_6H_9(C_3H_7)OH$; hexahydrothymol) also is only slightly soluble in alcohol, is fairly volatile, and in addition to any antiseptic properties provides a cooling, tingling sensation.

The essential oils are used in amounts effective to provide antimicrobial activity in the oral cavity. Generally, the total amount of essential oils present in a composition of this invention can be from about 0.001% to about 0.5% w/v, with about 0.16% to about 0.28% w/v being preferred. The compositions of the present invention contain thymol and one or more other essential oils. Preferably the additional essential oils are eucalyptol, menthol, or methyl salicylate, or mixtures thereof. Most preferably, the composition contains all four of these essential oils.

Thymol is preferably employed in amounts of from about 0.001% to about 0.5% w/v, and most preferably from about 0.04% to about 0.07% w/v. Eucalyptol may be employed in amounts of from about 0.001% to about 0.5% w/v, and preferably from about 0.085% to about 0.10% w/v. Menthol is preferably employed in amounts of from about 0.001% to about 0.5% w/v and most preferably from about 0.035% to about 0.05% w/v. Methyl salicylate is preferably employed in amounts of from about 0.001% to about 0.5% w/v, and most preferably from about 0.04% to about 0.07% w/v.

The mouthwash compositions of this invention provide effective antimicrobial activity without the presence of other types of antimicrobial compounds. For example, the compositions of this invention do not require known antimicrobial nitrogen-containing organic compounds, such as chlorhexidine gluconate and the like, to achieve effective antimicrobial activity. Thus, the reduced alcohol and alcohol-free peroxide containing mouthwash compositions of this invention are particularly advantageous over the compositions of the prior art.

Although not necessary, it is possible to employ other antimicrobial agents in the composition of this invention. Other exemplary antimicrobial agents include triclosan, cetyl pyridium chloride, domiphen bromide, quaternay ammonium salts, zinc compounds, sanguinanine soluble pyrophosphates, fluorides, alexidine, octonidine, EDTA, and the like.

The carrier for the essential oils (i.e., the active ingredients) is an aqueous medium. The aqueous medium may be a water-alcohol-surfactant mixture, generally water-ethanol-surfactant. Alternatively, in the case of alcohol-free compositions, the aqueous medium is a water-surfactant mixture. In the past, most antiseptic oral mouthwash compositions, such as Listerine®-brand mouthwashes, required high ethanol levels of up to about 27% v/v. These high levels were necessary to assist the actives in providing the necessary antimicrobial functionality as well as providing a clear, aesthetically attractive liquid medium. Merely reducing the alcohol levels, without more, results in a cloudy, less efficacious product.

Without being bound to any theory, it is believed that in these high alcohol level oral compositions, the alcohol solubilizes the antimicrobial actives and in so doing acts as an active enhancement mechanism. The actives are more readily dispersed throughout the solution and can attack pathogenic microbes throughout the oral cavity. Reducing the alcohol levels was believed to adversely affect this enhancement mechanism.

In accordance with a preferred embodiment of the present invention, however, it was surprisingly and unexpectedly found that alcohol may be used at reduced levels or may even be completely removed without sacrificing antimicrobial efficacy or clarity if the mouthwash composition also contains hydrogen peroxide and a surfactant. By "reduced level" of alcohol is meant an amount of ethanol up to about 22% v/v, preferably no more than about 10% v/v, and most preferably from about 0.1 to 10% v/v. By "alcohol-free" is meant that the composition is substantially free of ethanol.

The hydrogen peroxide in combination with at least one surfactant has been found to provide substantially equivalent and even enhanced antimicrobial activity of the essential oils for reduced alcohol and alcohol-free compositions compared to that exhibited by an antiseptic mouthwash having high alcohol levels on the order of about 27% v/v. A convenient reference point is the antimicrobial activity exhibited by a high alcohol level Listerine®-brand mouthwash; i.e., one which contains about 27% v/v ethanol. Expressed in terms of an "R-Factor," which, as explained below, represents the time necessary to effectively kill typical oral cavity microbes in an in vitro biofilm, normalized against the kill time exhibited in vitro by a 27% v/v Listerine®-brand mouthwash, the mouthwash compositions of this invention exhibit an R-Factor of less than about 2, preferably less than about 1.2, and most preferably less than about 1.0.

Surface active agents (surfactants) are employed in the compositions of this invention. They are organic materials which aid in the complete dispersion of the ingredients throughout the solution as well as dispersing the preparation throughout the oral cavity. Preferably, the surfactant used in the compositions of this invention is a non-ionic surfactant or anionic surfactant employed in an amount sufficient to help solubilize the actives. Mixtures of non-ionic surfactant and anionic surfactant may also be used. By sufficient amount it is meant that the surfactant is present in an amount that effectively assists in the solubilization of the essential oils.

The preferred non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25.

By way of example, non-ionic surfactants useful in this invention include the following poloxamers:

| 105 | 188 | 237 | 334 |
| 108 | 215 | 238 | 335 |
| 124 | 217 | 284 | 338 |
| 184 | 234 | 288 | 407 |
| 185 | 235 | 333 | |

Generally these polymers when used are present in amounts of from about 0.01% w/v to about 8.0% w/v, and preferably from about 0.25% to about 0.75% w/v. A particularly preferred poloxamer is poloxamer 407 which is incorporated in an amount of about 0.1 to 4.5% w/v.

The preferred anionic surfactants are selected from sodium lauryl sulfate, magnesium lauryl sulfate, zinc lauryl sulfate, Tauranol® and the like. Tauranol® is sodium-N-methyl-N-cocoyl taurate available from Finetex, N.J. Generally, the anionic surfactants when used are present in amounts of about 0.01% to about 1% w/v, and preferably from about 0.1% to about 0.5% w/v.

The surfactant is used to help solubilize the essential oils and flavor oils which may otherwise not be soluble in these aqueous systems due to their reduced ethanol content. The surfactant(s) also act to disperse the actives and flavors throughout the solution and enable the compositions to provide a clear, uniform appearance that is aesthetically more appealing.

The compositions of this invention may contain a mixture of a non-ionic surfactant and an anionic surfactant. An exemplary surfactant mixture, which is preferred, particularly when the composition is substantially free of ethanol, includes poloxamer 407 and sodium lauryl sulfate.

In one embodiment of this invention, three types of peppermint oil—natural, Far West (redistilled, terpeneless) and Rose Mitchum—are combined to provide a triple blend. This unique blend of flavor oils not only provides a pleasant tasting mouthwash but also serves to taste mask the bitter tasting essential oil actives discussed above. Each of these peppermint oils is present in substantially the same amount, from about 0.001% w/v to about 1.0% w/v, and preferably in an amount of from about 0.2% w/v to about 0.3% w/v. Combined, the triple blend is incorporated in the mouthwash composition in an amount of approximately 0.01% w/v to about 4.0 w/v, preferably in an amount of from about 0.5% w/v to about 0.9% w/v.

The essential oil methyl salicylate not only provides antimicrobial action but, being a wintergreen flavor oil, also adds to the organoleptic flavor tones and complements the taste masking function of the peppermint oil blend.

Other flavor oils may also be added to further modify or magnify the cooling minty taste of the peppermint, or reduce or mask the sharp "bite" or "burn" of ingredients such as thymol and ethanol. Suitable flavors (and typical amounts) include spearmint oil (from about 0.01% w/v to about 1% w/v), oil of anise (from about 0.01% w/v to about 0.2% w/v), benzyl alcohol (from about 0.001% w/v to about 0.5% wv) and anethole (from about 0.01% w/v to about 0.5% w/v). Other flavors such as citrus oils, vanillin, cooling compounds and the like may be incorporated to provide further taste variations.

The particular flavor oils and other taste-improving ingredients employed will vary depending upon the particular taste and feel desired. Those skilled in the art can select and customize these types of ingredients to provide the desired results.

Additional conventional components may be added as in mouthwashes of the prior art. Whereas some alcohol containing mouthwashes have a pH of about 7.0, reduction of the alcohol level, or its total elimination, requires the addition of preservatives which drops the pH to unacceptable levels. Buffer systems are then necessary to control the pH of the composition at optimal levels. This is generally accomplished through the addition of a weak acid and its salt or a weak base and its salt. Useful systems have been found to be sodium benzoate and benzoic acid in amounts of from about 0.01% to about 4.0% w/v, and sodium citrate and citric acid in amounts of from about 0.001% to about 0.2% w/v. Preferably the buffers are incorporated in amounts that maintain the pH at levels of from about 3.5 to about 7.5, and more preferably from about 4.0 to 5.0. Without being bound to any theory, it is believed that these pH levels provide the essential oils with an environment that also maximizes their antimicrobial activity.

Other conventional ingredients may be used in the mouthwash compositions of this invention, including those known and used in the art. For example, humectants such as polyethylene glycol may be added as an additional solubilizer for the flavor oils and to also provide texture to the composition. These are incorporated in amounts of from about 0.3% w/v to about 0.6% w/v, and preferably about 0.5% w/v. Softeners such as glycerin may be added to enhance the lubricous mouthfeel of the mouthwash as it is used and to provide a refreshing, moist, organoleptic feeling thereafter. Glycerin may be incorporated in amounts of from about 0.05% w/v to about 10.0% w/v, and preferably in an amount of about 7.5% w/v. Sweeteners such as aspartame or sodium saccharin and the like may be added for better taste in amounts of from about 0.005% w/v to about 1.0% w/v, and preferably in an amount of approximately 0.05% wv.

Zinc chloride or other zinc salts e.g. zinc gluconate, zinc sulfate etc., may be added as an astringent for an "antiseptic cleaning" feeling in an amount of from about 0.0025% w/v to about 0.200% w/v. And although the mouthwash formulations of this invention may be formulated to be substantially clear and colorless, acceptably approved food dyes are preferably used to provide a pleasing color to the formulations of the invention. These may be selected from the long list of acceptable food dyes and in particular may be incorporated to provide the spearmint green formulation discussed infra. Suitable dyes for this purpose include FD&C yellow #5, FD&C yellow #10 and FD&C green #3. These are added in conventional amounts, typically in total amounts of from about 0.0003% w/v to about 0.0005% w/v, and preferably from about 0.000035% wv to about 0.00045% w/v.

It is most preferable to prepare the mouthwash composition of this invention as a two-part mouthwash system. This is accomplished by preparing a base composition having the above described components with the exception of the peroxide. The peroxide is prepared as a separate aqueous solution. The concentration of the components in the base composition and the peroxide solution is dependent upon the ratio at which the base composition and peroxide will be mixed. The base composition and the peroxide solution are generally mixed at a ratio from about 1:10 to about 10:1 by volume. The preferred mixture ratio is 1:1 by volume. Once the ratio has been determined it is a simple arithmetic calculation to determine the concentration of the components in the base composition and the peroxide solutions which will result in the mouthwash composition of this invention after mixing at the predetermined ratio.

The two-part mouthwash system of this invention is comprised of (i) a first vessel containing a base composition comprising thymol and one or more other essential oils, optionally ethanol, at least one surfactant and water and (ii) a second vessel containing an aqueous peroxide solution, wherein after mixing an amount of said base composition with an amount of said peroxide solution a mouthwash composition is provided comprising (a) an antimicrobial effective amount of thymol and one or more essential oils; (b) optionally, ethanol in an amount up to about 30% v/v, preferably up to about 22%, most preferably up to about 10%; (c) from about 0.1 to about 8.0% w/v, preferably from about 0.1 to about 3.0% w/v peroxide; (d) at least one surfactant in an amount sufficient to solubilize said essential oils; and (e) water. The preferred ranges and components set forth for the mouthwash compositions of this invention are applicable to the calculation of the concentration of the components in the base compositions and peroxide solutions of the two-part mouthwash system of this invention.

The first and second vessels of the two-part mouthwash system may be separate containers or two compartments integrally united in a single container. If the vessels are separate containers, then base compositions and peroxide solutions may be mixed in another container prior to use simply by pouring in the predetermined ratio of the base composition and peroxide solution. On the other hand, if the base composition and peroxide solution are stored in an integrally united container, such a container may be designed so that the base composition and peroxide solution are mixed in an appropriate ratio as the mouthwash composition is dispensed from the container. Such a container may employ, for example, two channels, one from each vessel, which merge in a mixing chamber, and from which there is an outlet to dispense the mixed mouthwash composition. Or mixing can occur in another container. Such a device could preferably employ one-way valves in the channels to avoid contamination of the base composition and peroxide solution in the vessels. Other types of vessels and containers could also be employed in the two-part mouthwash system of this invention.

Water is added to q.s. the base composition and aqueous peroxide solution, and the base composition and aqueous peroxide solution may then be bottled and packaged for shipping. The mouthwash composition of the present invention may also be formulated, if desired, as gels, foams or pastes, using standard formulations known in the art as appropriate.

Alternatively, the base compositions of the present invention may be formulated in a chewing gum, semi-solid (paste, gel, foam), or liquid concentrate form. In such embodiments, for example, water is added to q.s. the volume to the necessary total for a semi-solid or liquid concentrate.

R-Factor

Biofilms of the microorganism *Streptococcus mutans* (ATCC #25175) grown on stainless steel wires simulate thick, semipermeable dental plaque. For purposes of the present invention, an "R-Factor" is a convenient measure of the antimicrobial efficacy of the mouthwash compositions of the present invention, as measured by their ability to kill those biofilms. The R-Factor is defined as the ratio of (1) the time, in minutes, necessary for a mouthwash composition to kill *S. mutans* microorganism biofilms grown in vitro on stainless steel wires, to (2) the time, in minutes, necessary for a standard high alcohol mouthwash composition to kill similar biofilms of the same microorganism grown in vitro on other, identical stainless steel wires. Those kill times are obtained by a plaque penetration assay developed by the present inventors.

Plaque Penetration Assay

The plaque penetration assay employed by the present inventors to obtain their biofilm critical kill times is a modification of the well-known procedure of Tanzer, et al., described or referenced in, e.g., Tanzer, et al., "Structural requirements of Guanide, Biguanide and Bisbiguanide Agents for Antiplaque Activity," *Antimicrobial Agents and Chemotherapy*, December 1977, pp. 721–729; and Tanzer, et al., "In Vitro Evaluation of Seven Cationic Detergents as Antiplaque Agents," *Antimicrobial Agents and Chemotherapy*, March 1979, pp. 408–414.

The high alcohol mouthwash composition employed by the present inventors as their standard for their plaque penetration assay contains 27% v/v ethanol and has the composition shown in the following Table 1:

TABLE 1

| Ingredient | Amount |
| --- | --- |
| Ethanol (USP) | 284 mls |
| Thymol | 0.639 gram |
| Eucalyptol | 0.922 gram |
| Menthol | 0.425 gram |
| Methyl Salicylate | 0.64 gram |
| Benzoic Acid | 1.5 grams |
| Caramel | 0.215 gram |

TABLE 1-continued

| Ingredient | Amount |
| --- | --- |
| Poloxamer 407 | 1.0 gram |
| Water | Q.S. to 1 Liter |

The media required for the plaque penetration assay include sterile deionized water; Letheen Broth (DIFCO); and Jordan's complex medium (with and without bromocresol purple pH indicator) [see Jordan, H. V. et al. *J. Dent. Res.* 39: 116–123 (1960)]. The equipment requirements for the assay include a large number of sterile glass test tubes (e.g., 13×100 millimeters); test tube racks to hold multiple rows of sample tubes; an autoclave; and stainless steel Nichrome wires (1.5×85 mm). It is convenient to attach each plaque wire to a Morton Closure (without fingers) by any suitable means, such as welding.

Jordan's medium may be prepared by blending the following ingredients with heating as necessary:

| Ingredient | Amount |
| --- | --- |
| Trypticase Peptone (BBL) | 5 grams |
| Yeast Extract | 5 grams |
| $K_2HPO_4$ | 5 grams |
| Stock Salts Solution (see below) | 0.5 ml |
| Sucrose | 50 grams |
| Sodium Carbonate | 0.05 grams |
| Deionized Water | Q.S to 1 Liter |

| Stock Salts Solution | |
| --- | --- |
| Ingredient | Concentration |
| $MgSO_4$(anhydrous) | 3.9 g/L |
| $FeCl_3 \cdot 6H_2O$ | 0.4 g/L |
| $MnCl_2$ (anhydrous) | 0.12 g/L |
| Distilled water | Q.S. to 1 Liter |

The pH is adjusted to 7.1 with 5N HCl followed by cooling to room temperature, if necessary. 50 ml is removed from the batch and placed in a 100 milliter flask. Jordan's medium with pH indicator ("recovery medium") is prepared by adding 1 ml of a 1% bromocresol purple stock solution (i.e., 0.1 gram bromocresol purple in 10 mls distilled water) to 1 liter of Jordan's medium.

The culture for the assay is prepared as follows. Upon receipt, the ATCC culture is rehydrated and subcultured according to the directions supplied by the American Type Culture Collection. The subculture is streaked for purity on Brain-Heart Infusion Agar (DIFCO) and inoculated into 100 ml of sterile BHI. The agar plates are examined for purity after 14–18 hours. If acceptable, 11 ml of sterile glycerin are added to the BHI culture, vortexed and then subdivided into 1.8 ml cryogenic tubes. The cultures are then stored at −80° C.

Four days prior to an assay, a frozen vial is thawed and added to the small, 100 ml flask containing 50 ml of Jordan's medium to start the cultures used for the biofilm assay. After 14–18 hours, the contents of the small flask are decanted aseptically into 2 liters of Jordan's medium. The resulting inoculated medium is then aseptically dispensed, in 5.0 ml portions, into a number of empty sterile test tubes, each tube having a plaque wire-quipped Morton cap. The inoculated tubes are then incubated anaerobically overnight (i.e., 14–16 hours) at 37° C.

The number of test tubes will vary depending upon the number of different mouthwash samples being tested, but it will be convenient to describe an assay of a standard high alcohol mouthwash and four reduced alcohol mouthwash samples, which requires racks each holding 75 test tubes (i.e., five rows of fifteen tubes, each row comprising five sets of three tubes each). The first set of three tubes in each row is usually reserved for the standard high alcohol mouthwash, with the succeeding four sets of three tubes each in that row being reserved for the four reduced alcohol samples. There are three tubes in each set because each assay is performed in triplicate.

After the overnight incubation, the plaque wires are then transferred into fresh Jordan's medium in 75 tubes (in a second rack) and again incubated anaerobically for 24 hours at 37° C. This procedure is repeated once more. Thus, the plaque wires are cultured for 3 days, with two transfers after initial inoculation.

On the third day, just prior to the assay, five additional racks (each containing 75 sterile test tubes) are prepared a first (assay) rack whose test tubes each contain 6 ml of the sample mouthwashes; a second (water) rack whose test tubes each contain 6 ml of sterile deionized water, third and fourth racks whose test tubes each contain 6 ml of Letheen broth rinse; and a fifth rack whose test tubes each contain 5 ml of Jordan's recovery medium. For convenience, the racks may be marked for test series identity and time (by row).

Assay Procedure: Each assay will involve triplicate testing at time points separated by one minute intervals, e.g., at 2, 3, 4, 5 and 6 minutes of mouthwash treatment. The first (or bottom) row of each rack corresponds to the first test time and the succeeding four rows correspond, respectively, to the next four test times. The exact time of exposure of the plaque wires to the sample mouthwashes can be varied according to the thickness of the "plaques;" ideally, the exposure period will result in positive microorganism growth in the first one or two sampling intervals of the high alcohol control group, (i.e., the first and second row) and no growth thereafter. Establishing lower and upper limits of exposure required for complete kill by the control mouthwash permits an accurate comparison of the four sample mouthwashes to this control. Mouthwash exposure takes place in a 37° C. New Brunswick shaking water bath (shake speed 3) and may be staggered so that the 5 time points are run concurrently, but with sufficient time to permit accurate timing and handling.

(1) To start assay, transfer one row of plaque wires to the first (bottom) row of tubes in the rack containing 6 ml of sterile water. Leave in place 2 minutes. Repeat for the next four rows of plaque wires.

(2) After the water rinse, transfer each row of plaque wires into the appropriate, corresponding, row of tubes in the rack containing 6 ml of test mouthwash. Leave each row of plaque wires in place, with shaking in the 37° water bath, for its treatment (exposure) period; i.e., remove the rows of plaque wires sequentially at 5 preset time points so that each succeeding row of plaque wires is exposed to a mouthwash for successively longer periods of time (e.g., 2, 3, 4, 5 and 6 minutes; individual timing can vary according to estimated "plaque" thickness.

(3) For each row of plaque wires, at the end of its treatment period, immediately remove the row and place it in the appropriate corresponding row of the first rack of 6 ml Letheen Broth neutralization/rinse tubes. Leave each row of wires in that broth for 5 minutes and then transfer it to the appropriate corresponding row of the second rack of 6 ml Letheen Broth rinse tubes.

(4) At the end of the second Letheen Broth rinse, remove each row of plaque wires and place it in the appropriate corresponding row of the rack of 6 ml Jordan's recovery medium (with bromocresol purple). Incubate anaerobically for 48 hours at 37° C.

(5) Read for growth (+) or no growth (−) at 24 and 48 hours. Positive growth is indicated by a color change from purple to yellow (i.e., if the microorganism is still viable, it will produce an acid which causes the color change); positive growth is often accompanied by an increase in broth turbidity.

Determination of Critical Kill Times and R-Factor: Since each mouthwash sample is located in the same set of three tubes in each row of the rack, the critical time necessary for the sample to completely kill the microorganism can be determined by observing the point (front to back or bottom to top, as the case may be) at which the Jordan recovery medium color changed from yellow to purple. The critical kill time for any sample, divided by the critical kill time for the control mouthwash in that same rack, gives the R-Factor for that sample.

Table 2 below summarizes a statistical scale developed by the present inventors which relates the observed change from growth (+) to no growth (−) to critical kill times. For example, as shown in the first row of Table 2, where the observed condition changes from growth (continuous +'s) to no growth (continuous −'s) ("no anomaly"), the critical kill time is determined by adding 0.50 minute to the time at which the last growth observation (+) was made. The balance of Table 2 sets forth how critical kill times are determined for different observed growth/no growth intervals between continuous growth segments and continuous no growth segments.

TABLE 2

BUSCH Scores For Critical Kill Times (CKT)

| Intervals between continuous +'s and −'s | Add To Last (+) Time |
| --- | --- |
| No anomaly | 0.50 |
| −+ | 1.50 |
| −++ | 2.90 |
| −+++ | 4.10 |
| −+−+ | 2.50 |
| −+−−+ | 2.10 |
| −++−+ | 4.06 |
| −−+ | 1.10 |
| −−++ | 2.50 |
| −−+−+ | 3.84 |
| −−−+ | 0.90 |
| −−−−+ | 0.80 |

By way of further example, consider the examples of growth/no growth sequences, and their associated critical kill times, in Table 3. In the first row of Table 3, there was no anomaly between continuous +'s and continuous −'s; therefore, CKT (per Table 2)=4.0+0.5=4.5 minutes i.e., kill occurred somewhere between 4.0 and 5.0 minutes). In the second row of Table 3, the interval between continuous +'s and continuous −'s is +; therefore, CKT (per Table 2)=2.0+ 1.5=3.5 minutes.

TABLE 3

Examples of Growth/No Growth Sequences and CKT

| Treatment Times (min) | | | | | |
| --- | --- | --- | --- | --- | --- |
| 2.0 | 3.0 | 4.0 | 5.0 | 6.0 | CKT |
| + | + | + | − | − | 4.5 |
| + | − | + | − | − | 3.5 |
| + | + | + | + | + | >6.5 |
| − | − | − | − | − | <2.0 |
| + | − | − | + | − | 3.1 |

In the case of rows 3 and 4 of Table 3, clearly no end point was reached. It is assumed here that kill will occur at some point in excess of 6.5 minutes (>6.5) or much below 2.0 minutes (<2.0), respectively.

Row 5 (Table 3) is an example where the kill scale is dependent on the values which are located to the left of the last + and to the right of the first −. For that particular example, CKT=2.0+1.1=3.1 minutes (per Table 2).

The following examples are provided to illustrate the present invention and its advantages. Throughout the examples, all percentages are stated as % w/v except where noted (e.g., ethanol contents are stated as % v/v).

EXAMPLE 1

A base composition was prepared having the following components in deionized water:

| Components | % w/v |
| --- | --- |
| Thymol | 0.128 |
| Menthol | 0.035 |
| Methyl salicylate | 0.128 |
| Eucalyptol | 0.184 |
| Ethanol (USP) | 20.0 (v/v) |
| Sodium Lauryl Sulfate | 0.6 |
| $MgSO_4$ | 0.6 |

This base composition (100 ml) was prepared in the following manner. First, 21.05 ml ethanol (USP) was transferred to a beaker and then 0.6 g sodium lauryl sulfate and 0.6 g $MgSO_4$ were added with stirring. Next, 0.1844 g eucalyptol, 0.1278 g thymol, 0.085 g menthol and 0.128 g methyl salicylate were added to the mixture, followed by the addition of deionized water to bring the composition to a volume of 90 ml. Therafter, the pH was adjusted to 4.2 with 0.1N HCl, 0.1 N NaOH, or a suitable buffer e.g. sodium benzoate/benzoate acid and the composition q.s. to 100 ml with deionized water to obtain the base composition.

EXAMPLE 2

Three peroxide solutions were prepared in deionized water having the following composition:

| | Concentration (% w/v) | | |
| --- | --- | --- | --- |
| Component | Solution A | Solution B | Solution C |
| $H_2O_2$ | 2.0 | 4.0 | 5.8 |
| Benzoic Acid | 0.3 | 0.3 | 0.3 |

Solution A was prepared by adding 0.3 g benzoic acid to 6.67 ml of a 30% hydrogen peroxide solution in water. The solution was q.s. to 90 ml with water and the pH adjusted to 4.2 with 0.1 N HCl or 0.1N NaOH. After adjusting the pH, the solution was q.s. to 100 ml with deionized water to obtain aqueous peroxide solution A. Solutions B and C were prepared in a similar manner, except that 13.33 ml and 19.33 ml of 30% hydrogen peroxide solution in water, respectively, were used to prepare each solution.

EXAMPLE 3

A peroxide containing reduced alcohol mouthwash composition (1/A) was prepared by mixing equal volume portions of the base composition prepared in Example 1 with the peroxide solution A prepared in Example 2. Two other peroxide containing reduced alcohol mouthwash compositions 1/B and 1/C, respectively) were prepared in a similar manner using peroxide solutions B and C prepared in Example 2. The resulting compositions are described in Table 4.

TABLE 4

| Component | Base Composition/Peroxide Solution % w/v | | |
|---|---|---|---|
| | 1/A | 1/B | 1/C |
| Thymol | 0.064 | 0.064 | 0.064 |
| Menthol | 0.043 | 0.043 | 0.043 |
| Methyl salicylate | 0.064 | 0.064 | 0.064 |
| Eucalyptol | 0.092 | 0.092 | 0.092 |
| Ethanol (% v/v) | 10.0 | 10.0 | 10.0 |
| Sodium Lauryl Sulfate | 0.3 | 0.3 | 0.3 |
| $MgSO_4$ | 0.3 | 0.3 | 0.3 |
| $H_2O_2$ | 1.0 | 2.0 | 2.9 |
| Benzoic Acid | 0.15 | 0.15 | 0.15 |
| Deionized Water | q.s. | q.s. | q.s. |

EXAMPLE 4

A of base composition were prepared in a manner similar to Example 1. The concentration of the components of those compositions in deionized water are set forth in Table 5 below.

TABLE 5

| Components | % w/v | | | | |
|---|---|---|---|---|---|
| | 4a | 4b | 4c | 4d | 4e |
| Thymol | 0.128 | 0.128 | 0.128 | 0.128 | 0.128 |
| Menthol | 0.085 | 0.085 | 0.085 | 0.085 | 0.085 |
| Methyl Salicylate | 0.128 | 0.128 | 0.128 | 0.128 | 0.128 |
| Eucalyptol | 0.184 | 0.184 | 0.184 | 0.184 | 0.184 |
| Ethanol (% v/v) | 10.0 | 10.0 | — | 10.0 | 1.0 |
| Sodium Lauryl Sulfate | 0.6 | — | — | — | — |
| Pluronic ® F127[1] | — | 0.6 | 0.9 | — | — |
| Tauranol ® [2] | — | — | — | 0.6 | 0.6 |
| $MgSO_4$ | 0.6 | 0.6 | 0.6 | 0.6 | 0.6 |
| Benzoic Acid | 0.3 | 0.3 | 0.3 | 0.3 | 0.3 |
| Deionized Water | q.s. | q.s. | q.s. | q.s. | q.s. |

[1]Pluronic ® F-127 is poloxamer 407 available from BASF
[2]Tauranol ® is sodium-N-methyl-N-cocoyl taurate available from Finetex, New Jersey The preparation of these base compositions is described with more particularity below. Base composition 4a was prepared by transferring 10.53 ml of ethanol (USP) to a beaker, followed by the addition with stirring of 0.06 g sodium lauryl sulfate, 0.6 g $MgSO_4$ and 0.3 g benzoic acid. To this mixture was added 0.1844 g eucalyptol, 0.1278 g thymol, 0.085 g menthol and 0.128 g methyl salicylate. The composition was then q.s. to 90 ml with deionized water, the pH adjusted to 4.2 and then q.s. to 100 ml with deionized water to obtain base composition 4a. Base composition 4b was prepared in a similar manner, with the exception that 0.6 g Pluronic® F127 was substituted for the sodium lauryl sulfate.

The base composition having no alcohol (4c) was prepared by transferring 75 ml deionized water to a beaker, followed by adding with stirring 0.9 g Pluronic® F127, 0.6 g $MgSO_4$ and 0.3 g benzoic acid. The identical essential oils employed in base compositions 4a and 4b were then added, the solution was q.s. to 90 ml by adding dionized water, the pH adjusted to 4.2 and the solution q.s. to 100 ml with deionized water to obtain base composition 4c.

Two base compositions containing the anionic surfactant Tauranol® were prepared. Base composition 4d was prepared in a manner similar to base composition 4a with the exception that 0.6 g Tauranol® was substituted for sodium lauryl sulfate. Base composition 4e was prepared in a manner similar to base composition 4d, except that 1.05 ml of ethanol (USP) was used instead of 10.53 ml.

EXAMPLE 5

Two peroxide solutions were prepared in deionized water having the following composition:

| Solution D | Solution E |
|---|---|
| 4.0% w/v $H_2O_2$ | 5.8% w/v $H_2O_2$ |

Solutions D and E were prepared by adding 13.33 ml and 19.33 ml, respectively, of a 30% hydrogen peroxide solution to a beaker and bringing the total volume of each solution to 90 ml with deionized water. Each solution was then adjusted to a pH of 4.2 with 0.1 N HCl or 0.1N NaOH and then each solution was q.s. to 100 ml by adding deionized water to obtain aqueous peroxide solutions D and E.

EXAMPLE 6

A series of peroxide containing reduced alcohol or alcohol-free mouthwash compositions were prepared using the base compositions for Example 4 and the peroxide solutions of Example 5. Each mouthwash composition was prepared by mixing equal volume amounts of a base composition and a peroxide solution. The resulting compositions are described in Table 6.

TABLE 6

| Components | Base Composition/Peroxide Solution (% w/v) | | | | | | | | | |
|---|---|---|---|---|---|---|---|---|---|---|
| | 4a/D | 4a/E | 4b/D | 4b/E | 4c/D | 4c/E | 4d/D | 4d/E | 4d/D | 4d/E |
| Thymol | 0.064 | 0.064 | 0.064 | 0.064 | 0.064 | 0.064 | 0.064 | 0.064 | 0.064 | 0.064 |
| Menthol | 0.043 | 0.043 | 0.043 | 0.043 | 0.043 | 0.043 | 0.043 | 0.043 | 0.043 | 0.043 |
| Methyl Salicylate | 0.064 | 0.064 | 0.064 | 0.064 | 0.064 | 0.064 | 0.064 | 0.064 | 0.064 | 0.064 |
| Eucalyptol | 0.092 | 0.092 | 0.092 | 0.092 | 0.092 | 0.092 | 0.092 | 0.092 | 0.092 | 0.092 |
| Ethanol (USP) (% v/v) | 5.0 | 5.0 | 5.0 | 5.0 | — | — | 5.0 | 5.0 | 0.5 | 0.5 |
| Sodium Lauryl Sulfate | 0.3 | 0.3 | — | — | — | — | — | — | — | — |
| Pluronic ® F127 | — | — | 0.3 | 0.3 | 0.45 | 0.45 | — | — | — | — |
| Tauranol ® | — | — | — | — | — | — | 0.3 | 0.3 | 0.3 | 0.3 |
| $MgSO_4$ | 0.3 | 0.3 | 0.3 | 0.3 | 0.3 | 0.3 | 0.3 | 0.3 | 0.3 | 0.3 |
| Benzoic Acid | 0.15 | 0.15 | 0.15 | 0.15 | 0.15 | 0.15 | 0.15 | 0.15 | 0.15 | 0.15 |
| $H_2O_2$ | 2.0 | 2.9 | 2.0 | 2.9 | 2.0 | 2.9 | 2.0 | 2.9 | 2.0 | 2.9 |

The peroxide containing reduced alcohol mouthwash compositions of this invention were tested for plaque penetration efficacy. Each of the mouthwash compositions of Table 4 and 6 were evaluated in vitro for its ability to kill microorganisms in a biofilm, using the protocol described above. The results are shown below in Table 7, which also shows the percentages of ethanol, $H_2O_2$ and surfactant in those compositions.

TABLE 7

| Mouthwash Composition | Ethanol % v/v | $H_2O_2$ % w/v | Surfactant % w/v | Average CKT (Min) Composition | Average CKT (Min) Control | R Factor |
|---|---|---|---|---|---|---|
| 1/A | 10.0 | 1.0 | 0.3 (S) | 5.25 | 3.17 | 1.66 |
| 1/B | 10.0 | 2.0 | 0.3 (S) | 3.25 | 3.17 | 1.02 |
| 1/C | 10.0 | 2.9 | 0.3 (S) | <3 | 3.17 | <0.9 |
| 4a/D | 5.0 | 2.0 | 0.3 (S) | 3.25 | 3.92 | 0.83 |
| 4a/E | 5.0 | 2.9 | 0.3 (S) | 3.58 | 3.92 | 0.91 |
| 4b/D | 5.0 | 2.0 | 0.3 (P) | 3.25 | 3.35 | 0.97 |
| 4b/E | 5.0 | 2.9 | 0.3 (P) | 2.58 | 3.35 | 0.77 |
| 4c/D | — | 2.0 | 0.45 (P) | 3.58 | 3.35 | 1.07 |
| 4c/E | — | 2.9 | 0.45 (P) | 3.58 | 3.35 | 1.07 |
| 4d/D | 5.0 | 2.0 | 0.3 (T) | 3.25 | 4.25 | 0.76 |
| 4d/E | 5.0 | 2.9 | 0.3 (T) | 2.25 | 4.25 | 0.53 |
| 4e/D | 0.5 | 2.0 | 0.3 (T) | 3.25 | 4.25 | 0.76 |
| 4e/E | 0.5 | 2.9 | 0.3 (T) | 2.25 | 4.25 | 0.53 |

S—Sodium Lauryl Sulfate
P—Pluronic ® F127
T—Tauranol ®

The results show that mouthwash compositions of this invention even having no alcohol exhibited plaque penetration activity substantially equivalent to the high alcohol containing control. When preferred amounts of hydrogen peroxide were used, the efficacy of the mouthwash composition was in some cases substantially better than that of the control, even at alcohol levels as low as 0.5% v/v.

Kill Kinetics Assays

The kill kinetics of several hydrogen peroxide aqueous solutions were assayed along with high alcohol containing control and a sterile water control. Kill Kinetics assays were performed by determining the growth of microorganisms after time (0.5, 1, 2, 5, and 10 minutes) exposure to test product. Neutralizing media was inoculated and incubated for 48 to 72 hours and growth/no growth recorded. The effect of biological fluids on the kill kinetics assay was determined by performing the assay with inoculum of each microorganism prepared in heat inactivated horse serum
Microorganisms Cultures of all microorganisms were obtained from the American Type Culture Collection (ATC), Rockville, Md., reconstituted, aliquoted and maintained by freezing at −100° C. over liquid nitrogen. All aerobes were cultivated a 37° C., with the exception of *Candida albicans* which was cultivated at 30° C., and all anaerobes were cultivated at 37° C., under an anaerobic atmosphere.

Preparation of Microorganisms

The test organisms were transferred from frozen stock cultures and passed at least 3 time in modified Schaedler's broth and maintained by serial passage. For all tests, fresh cultures in late log or early stationary phase were used for inoculating. Faster growing cultures were used 16–24 hours after incubation, while some slower growing species required 2–3 days of incubation. Microorganisms were incubated either aerobically (37° C.) or anaerobically (37° C.).

Media

Growth Media

All cultures were grown in Schaedler broth (Difco or BBL) supplemented with 1 $\mu$g/ml soluble menadione (Sigma Chemical Co. #M5750), dispensed and sterilized by autoclaving.

Test Media

Neutralizing broth was comprised of modified Schaedler broth supplemented with Azolectin and Tween 80. The neutralizing broth was prepared by dissolving 28.4 grams of Schaedler broth in 900 ml of water. Soluble menadione was added to give a final concentration of 1 $\mu$g/m. Then 15 ml of the Neutralizing stock solution was added and the solution was q.s. to 1 liter with distilled water. The media was dispensed into test tubes and autoclaved.

The Neutralizing stock solution was prepared as follows: 35 grams of Azolictin (L-α-Phosphatidylcholine) was combined with 700 ml of distilled water. This was mixed and heated until the Azolectin was dissolved. Tween 80 (Polysorbate 80 NF) (250) grams) and potassium phosphate buffer (1 ml ) were added. The solution was mixed and heated until dissolution was complete. When the stock became clear it was q.s. to 1 liter and cooled to room temperature. The pH was adjusted to 7.2 with 1 N NaOH. The solution was aliquoted into glass containers, autoclaved and stored a 4° C.

Potassium phosphate buffer was prepared by dissolving 3.74 grams of $KH_2PO_4$ in 900 ml of distilled water. The pH was adjusted to 7.2 and q.s. to 1000 ml with distilled water.

Neutralizing Test

To assume adequate product neutralization a Neutralizing test was performed on each organism at the time of a kill kinetics assay. Each product (0.1 ml) was added to 10 ml of Test Neutralizing media. Each tube was inoculated with 0.1 ml of a 1:100 dilution of a standard inoculum of each organism in growth media. The diluted inoculum was used within 15 minutes of preparation. The tubes were incubated for 48 hours under the appropriate growth conditions and examined for growth by visual observation.

Kill Time Determination

Five hundred µl of inoculum of each test organism were inoculated into 4.5 ml of test product. Using a stop watch to time the test, a 0.5 ml aliquot of the reaction mixture was removed at 0.5, 1, 2, 5 and 10 minutes, added to 4.5 ml of fresh neutralizing test medium, mixed and incubated at 37° C. (except for C. albicans which was incubated at 30° C.) for 48 to 72 hours. After incubation the tubes were examined for growth by visual observation.

Inoculation was accomplished with the aid of a Matrix Technologies Programmable Electrapette (supplied by Warner Lambert). Six tubes were inoculated simultaneously. Each assay consisted of inoculating one tube of each test product. All assays were performed three times in duplicate, using a separate inoculum preparation.

Kill Time Determination—Effect of Biological Fluids on Inhibition

Heat activated horse serum (Gibco) was used to determine the effect of biological fluids upon antiseptic efficacy. Equal volumes of serum and each test organism were mixed and used as the inoculum. One ml was inoculated in 4 ml of test product. The kill time determination assay was then performed by inoculation of test medium followed by incubation as described above.

Each assay was done three times in duplicate.

Culture Monitoring

All cultures were monitored for purity by periodic transfer to Blood agar plates and selective media if appropriate. Cultures were checked for purity by visual observation of colonial morphology after an appropriate incubation period of 48 hours to 5 days.

Media Monitoring

Tubes of all media without test agent were inoculated with the appropriate organism to be assayed to serve as a positive control for growth. Tubes of uninoculated media from each batch of media prepared were also incubated to serve as a negative control for sterility.

Interpretation of Results

Results were recorded as the first time the inoculated tube exhibited no growth (i.e., the minimum time required to completely kill the test organisms). The summary critical kill time was recorded as the first point at which three or more of the six subculture tubes exhibited no growth. All tests in which three tubes showed growth were repeated for confirmation.

The results of the assay are set forth in Table 8 below.

TABLE 8

Kill Kinetics Assay w/Serum

|  | F. nucleatum #10953 | S. aureus #6538 | C. albicans #18804 |
|---|---|---|---|
| 0.5% $H_2O_2$ | <0.5 | >5.0 | >5.0 |
| 1.0% $H_2O_2$ | <0.5 | <0.5 | >5.0 |
| 1.5% $H_2O_2$ | <0.5 | <1.0 | <5.0 |
| Listerine | <0.5 | <1.0 | <0.5 |
| Sterile water | >5.0 | >5.0 | >5.0 |

This assay indicates the hydrogen peroxide aqueous solutions are not alone broad spectrum antiseptic and therefore the antiplaque efficacy of a combination of hydrogen peroxide and antimicrobial effective amounts of thymol and one or more other essential oils was not predictable.

EXAMPLE 7

A series of peroxide containing reduced alcohol or alcohol-free mouthwash compositions were prepared. Each composition was prepared by mixing a solution containing the essential oils, thymol, menthol, methyl salicylate and eucalyptol, the listed surfactants and ethanol, if preset, with an aqueous peroxide solution. The resulting mouthwash composition contained 0.064% w/v thymol, 0.043% w/v menthol 0.065% w/v methyl salicylate and 0.092% w/v eucalyptol. The concentration of the ethanol, peroxide and surfactants in the mouthwash composition as well as the plaque kill activity expressed as an R factor (as described above) are set forth in Table 9 below.

| Composition | Ethanol (% v/v) | $H_2O_2$ (% w/v) | SLS[1] (% w/v) | F127[2] (% w/v) | Plaque Kill Activity (R factor) |
|---|---|---|---|---|---|
| 7A | 0 | 0.5 | 0.2 | 1.0 | >1.3 |
| 7B | 0 | 1.0 | 0.2 | 1.0 | 1.1 |
| 7C | 0 | 1.5 | 0.2 | 1.0 | 0.7 |
| 7D | 0 | 1.5 | 0.25 | 1.0 | 1.0 |
| 7E | 0 | 0.5 | 0.3 | 1.0 | >1.4 |
| 7F | 0 | 1.0 | 0.3 | 1.0 | 1.2 |
| 7G | 0 | 1.5 | 0.3 | 1.0 | 0.8 |
| 7H | 0 | 1.5 | 0.25 | 1.0 | 1.2 |
| 7I | 10 | 0.5 | 0.20 | 0.20 | >1.4 |
| 7J | 10 | 1.0 | 0.20 | 0.20 | 1.1 |
| 7K | 10 | 1.5 | 0.20 | 0.20 | 0.8 |
| 7L | 10 | 1.5 | 0.25 | 0.20 | 0.8 |

[1]Sodium Lauryl Sulfate
[2]Pluronic ® 127 is poloxamer 407 available from BASF

The results indicate that the reduced alcohol and alcohol-free compositions containing about 1.0 to about 1.5% w/v hydrogen peroxide are highly effective antimicrobial compositions. Particularly preferred compositions are (i) the alcohol free composition containing about 0.3% w/v sodium lauryl sulfate and about 1.0% poloxame 407, and (ii) the reduced alcohol composition containing about 0.20% w/v sodium lauryl sulfate and about 0.20% w/h poloxamer 407.

What is claimed is:

1. A peroxide-containing two-part mouthwash system comprising: (i) a first vessel containing a base composition comprising an essential oil mixture comprising thymol, eucalyptol, menthol and methylsalicylate, optionally ethanol, at least one anionic surfactant and water and (ii) a second vessel containing an aqueous peroxide solution such that the aqueous peroxide solution is isolated from essential oils capable of reacting with the aqueous peroxide solution, wherein the contents of the first vessel and the second vessel can be dispensed and mixed into a separate container or compartment just prior to use, forming a mouthwash solution comprising: (a) from about 0.16 to about 0.5% of an essential oil mixture comprising: thymol, eucalyptol, menthol and methylsalicylate; (b) optionally, ethanol in an amount up to about 30% v/v; (c) from about 0.1% to about 8.0% w/v of a peroxide; (d) a sufficient amount of at least one anionic surfactant to assist in the solubilization of said essential oils; and (e) water.

2. A The peroxide-containing two-part mouthwash system of claim 1, wherein the amount of ethanol in said antimicrobial composition is no more than about 22% v/v.

3. The peroxide-containing two-part mouthwash system of claim 1, wherein the amount of ethanol in said antimicrobial composition is no more than about 10% v/v.

4. The peroxide-containing two-part mouthwash system of claim 3, wherein the peroxide in said antimicrobial composition is hydrogen peroxide present in an amount from about 0.1% to about 3.0% w/v.

5. The peroxide-containing two-part mouthwash system of claim 4, wherein the amount of hydrogen peroxide in said antimicrobial composition is from about 0.1% to about 2.9% w/v.

6. The peroxide-containing two-part mouthwash system of claim 4, wherein the surfactant is selected from the group consisting of non-ionic surfactants, anionic surfactants and mixtures thereof.

7. The peroxide-containing two-part mouthwash system of claim 6, wherein the surfactant is at least one non-ionic surfactant.

8. The peroxide-containing two-part mouthwash system of claim 7, wherein said non-ionic surfactant is selected from the group consisting of poloxamers.

9. The peroxide-containing two-part mouthwash system of claim 8, wherein the amount of poloxamer in said antimicrobial composition is from about 0.01% to about 1.0% w/v.

10. The peroxide-containing two-part mouthwash system of claim 9, wherein said poloxamer is Poloxamer 407.

11. The peroxide-containing two-part mouthwash system of claim 6, wherein the surfacant is at least one anionic surfactant.

12. The peroxide-containing two-part mouthwash system of claim 11, wherein said anionic surfactant is selected from the group consisting of sodium lauryl sulfate, magnesium lauryl sulfate and sodium N-methyl-N-cocoyl taurate.

13. The peroxide-containing two-part mouthwash system of claim 12, wherein the amount of said anionic surfactant in said antimicrobial composition is from about 0.01% to about 1.0% w/v.

14. The peroxide-containing two-part mouthwash system of claim 1, wherein an amount of thymol in said antimicrobial composition is from about 0.001% to about 0.5% w/v.

15. The peroxide-containing two-part mouthwash system of claim 14, wherein said antimicrobial composition contains eucalyptol in an amount of from about 0.001% to about 0.5% w/v, menthol in an amount of from about 0.001% to about 0.5% w/v, and methyl salicylate in an amount of from about 0.001% to about 0.5% w/v.

16. The peroxide-containing two-part mouthwash system of claim 1, wherein the amount of said base composition to be mixed with the amount of said peroxide solution is a ratio of about 1:10 to about 10:1.

17. The peroxide-containing two-part mouthwash system of claim 16, wherein the ratio of base composition to peroxide solution in said antimicrobial composition is about 1:1.

18. The peroxide-containing two-part mouthwash system of claim 1, wherein said first vessel and said second vessel are integrally united.

19. The peroxide-containing two-part mouthwash system of claim 1, wherein an R-Factor of said antimicrobial composition is less than about 1.2.

20. The peroxide-containing two-part mouthwash system of claim 1, wherein an R-Factor of said antimicrobial composition is less than about 1.0.

* * * * *